United States Patent
Hwang et al.

(10) Patent No.: US 8,048,064 B2
(45) Date of Patent: Nov. 1, 2011

(54) METHOD OF CURING INFLAMMATORY ACNE BY USING CARBON LOTION AND PULSED LASER

(75) Inventors: Hae Lyung Hwang, Goyang-si (KR); Sung Huan Gong, Seoul (KR); Jing Mei Li, Uijeongbu-Si (KR)

(73) Assignee: Lutronic Corporation (KR)

( * ) Notice: Subject to any disclaimer, the term of this patent is extended or adjusted under 35 U.S.C. 154(b) by 729 days.

(21) Appl. No.: 12/158,350

(22) PCT Filed: May 29, 2006

(86) PCT No.: PCT/KR2006/002043
§ 371 (c)(1),
(2), (4) Date: Jun. 20, 2008

(87) PCT Pub. No.: WO2007/073024
PCT Pub. Date: Jun. 28, 2007

(65) Prior Publication Data
US 2008/0319431 A1    Dec. 25, 2008

(30) Foreign Application Priority Data
Dec. 23, 2005 (KR) .................. 10-2005-0128505

(51) Int. Cl.
*A61B 18/20* (2006.01)
(52) U.S. Cl. ............................. 606/9; 128/898
(58) Field of Classification Search ....... 606/9; 128/898
See application file for complete search history.

(56) References Cited

U.S. PATENT DOCUMENTS

| | | |
|---|---|---|
| 5,112,328 A | 5/1992 | Taboada et al. |
| 5,312,396 A | 5/1994 | Feld et al. |
| 5,662,590 A | 9/1997 | de la Torre et al. |
| 5,707,401 A | 1/1998 | Talmore |
| 5,766,214 A | 6/1998 | Mehl, Sr. et al. |
| 5,843,071 A | 12/1998 | Bath |
| 5,873,875 A | 2/1999 | Altshuler |
| 5,885,211 A | 3/1999 | Eppstein et al. |
| 5,919,186 A | 7/1999 | Bath |
| 5,984,916 A | 11/1999 | Lai |
| 6,063,108 A | 5/2000 | Salansky et al. |
| 6,096,031 A | 8/2000 | Mitchell et al. |
| 6,149,671 A | 11/2000 | Nordquist et al. |
| 6,200,309 B1 | 3/2001 | Rice et al. |
| 6,242,477 B1 | 6/2001 | Okamoto et al. |
| 6,267,755 B1 | 7/2001 | Clementi et al. |
| 6,277,111 B1 | 8/2001 | Clement et al. |

(Continued)

FOREIGN PATENT DOCUMENTS

| | | |
|---|---|---|
| JP | 6190071 A | 7/1994 |
| JP | 2003300684 | 10/2003 |
| JP | 2003310639 | 11/2003 |

(Continued)

*Primary Examiner* — Henry M Johnson, III
*Assistant Examiner* — Jeffrey Lipitz
(74) *Attorney, Agent, or Firm* — Pepper Hamilton LLP

(57) ABSTRACT

Disclosed is a method of curing inflammatory acne by applying a carbon lotion onto a face covered with acne, irradiating the applied carbon lotion with a laser pulse having a pulse width of microsecond, and irradiating the applied carbon lotion with a laser pulse having a pulse width of nanosecond to sterilize acne bacilli and open skin pores clogged with sebum, thereby entirely treating the inflammatory acne. The method includes applying the carbon lotion onto epidermis to be cured and pores, irradiating the carbon lotion with a laser pulse to heat and burst the applied carbon lotion. With the method, the inflammatory acne is simply cured without scar.

5 Claims, 4 Drawing Sheets

U.S. PATENT DOCUMENTS

| | | |
|---|---|---|
| 6,379,376 B1 | 4/2002 | Lubart |
| 6,387,089 B1 | 5/2002 | Kreindel et al. |
| 6,494,900 B1 | 12/2002 | Salansky et al. |
| 6,524,329 B1 | 2/2003 | Benedict |
| 6,530,915 B1 | 3/2003 | Eppstein et al. |
| 6,595,986 B2 | 7/2003 | Almeida |
| 6,605,080 B1 | 8/2003 | Altshuler et al. |
| 6,607,523 B1 | 8/2003 | Asah et al. |
| 6,613,040 B2 | 9/2003 | Tankovich et al. |
| 6,676,655 B2 | 1/2004 | McDaniel |
| 6,685,730 B2 | 2/2004 | West et al. |
| 6,770,069 B1 | 8/2004 | Hobart et al. |
| 6,786,899 B1 | 9/2004 | Lai |
| 6,936,044 B2 | 8/2005 | McDaniel |
| 6,962,584 B1 | 11/2005 | Stone et al. |
| 6,997,923 B2 | 2/2006 | Anderson et al. |
| 7,041,093 B2 | 5/2006 | Toftkjaer |
| 7,097,656 B1 | 8/2006 | Akopov et al. |
| 7,101,384 B2 | 9/2006 | Benedict |
| 7,108,692 B2 | 9/2006 | Frenz et al. |
| 7,160,289 B2 | 1/2007 | Cohen |
| 7,282,060 B2 | 10/2007 | DeBenedictis et al. |
| 7,283,576 B2 | 10/2007 | Krupke |
| 7,306,620 B2 | 12/2007 | Cumbie |
| 7,309,335 B2 | 12/2007 | Altshuler et al. |
| 7,329,252 B1 | 2/2008 | Yamazaki et al. |
| 7,331,953 B2 | 2/2008 | Manstein et al. |
| 7,351,241 B2 | 4/2008 | Bendett et al. |
| 7,351,252 B2 | 4/2008 | Altshuler et al. |
| 7,353,829 B1 | 4/2008 | Wachter et al. |
| 7,354,448 B2 | 4/2008 | Altshuler et al. |
| 2001/0001118 A1 | 5/2001 | Asah et al. |
| 2001/0050083 A1 | 12/2001 | Marchitto et al. |
| 2002/0019624 A1 | 2/2002 | Clement et al. |
| 2002/0103482 A1 | 8/2002 | Scholler et al. |
| 2002/0107509 A1* | 8/2002 | Neuberger et al. ............... 606/9 |
| 2002/0161357 A1 | 10/2002 | Anderson et al. |
| 2003/0004556 A1 | 1/2003 | McDaniel |
| 2003/0023283 A1 | 1/2003 | McDaniel |
| 2003/0216719 A1 | 11/2003 | Debenedictis et al. |
| 2004/0093042 A1 | 5/2004 | Altshuler et al. |
| 2004/0162596 A1 | 8/2004 | Altshuler et al. |
| 2004/0167500 A1 | 8/2004 | Weekwerth et al. |
| 2004/0199152 A1 | 10/2004 | Key |
| 2004/0199223 A1 | 10/2004 | Anderson et al. |
| 2004/0225339 A1 | 11/2004 | Yaroslavsky et al. |
| 2004/0230258 A1 | 11/2004 | Altshuler et al. |
| 2004/0243111 A1 | 12/2004 | Bendett et al. |
| 2005/0004632 A1 | 1/2005 | Benedict |
| 2005/0015123 A1 | 1/2005 | Paithankar |
| 2005/0049582 A1 | 3/2005 | DeBenedictis et al. |
| 2005/0049658 A1 | 3/2005 | Connors |
| 2005/0119642 A1 | 6/2005 | Grecu et al. |
| 2005/0154380 A1 | 7/2005 | DeBenedictis et al. |
| 2005/0154381 A1 | 7/2005 | Altshuler et al. |
| 2005/0203495 A1 | 9/2005 | Malak |
| 2005/0215987 A1 | 9/2005 | Slatkine |
| 2005/0222555 A1 | 10/2005 | Manstein et al. |
| 2005/0251231 A1 | 11/2005 | Goldberg |
| 2006/0020309 A1 | 1/2006 | Altshuler et al. |
| 2006/0079947 A1 | 4/2006 | Tankovich et al. |
| 2006/0095095 A1 | 5/2006 | Cao |
| 2006/0095096 A1 | 5/2006 | DeBenedictis et al. |
| 2006/0189967 A1 | 8/2006 | Masotti et al. |
| 2006/0217787 A1 | 9/2006 | Olson et al. |
| 2006/0253178 A1 | 11/2006 | Masotti |
| 2006/0259102 A1 | 11/2006 | Slatkine |
| 2007/0005120 A1 | 1/2007 | Villacampa et al. |
| 2007/0027441 A1 | 2/2007 | Almeida |
| 2007/0032847 A1 | 2/2007 | Weckwerth et al. |
| 2007/0073367 A1 | 3/2007 | Jones et al. |
| 2007/0078500 A1 | 4/2007 | Ryan et al. |
| 2007/0123844 A1 | 5/2007 | Henry |
| 2007/0198068 A1 | 8/2007 | Chan et al. |
| 2007/0219601 A1 | 9/2007 | Neuberger |
| 2007/0260229 A1 | 11/2007 | Navarro et al. |
| 2008/0015554 A1 | 1/2008 | Cole et al. |
| 2008/0015556 A1 | 1/2008 | Chan et al. |
| 2008/0015557 A1 | 1/2008 | Chan et al. |
| 2008/0033516 A1 | 2/2008 | Altshuler et al. |
| 2008/0045933 A1 | 2/2008 | Perl |
| 2008/0058783 A1 | 3/2008 | Altshuler et al. |
| 2008/0058784 A1 | 3/2008 | Manstein et al. |
| 2008/0058904 A1 | 3/2008 | Hillis et al. |
| 2008/0091179 A1 | 4/2008 | Durkin et al. |
| 2008/0147052 A1 | 6/2008 | Bendett et al. |
| 2008/0154344 A1 | 6/2008 | Trusty et al. |
| 2008/0183250 A1 | 7/2008 | Tanojo et al. |
| 2008/0208178 A1 | 8/2008 | DeBenedictis et al. |
| 2008/0208179 A1 | 8/2008 | Chan et al. |
| 2008/0215040 A1 | 9/2008 | Paithankar et al. |
| 2008/0234786 A1 | 9/2008 | Cumbie |
| 2008/0262577 A1 | 10/2008 | Altshuler et al. |
| 2009/0146086 A1* | 6/2009 | Manstein .................. 250/504 R |

FOREIGN PATENT DOCUMENTS

| | | |
|---|---|---|
| JP | 2005034609 A | 2/2005 |
| KR | 2005051095 A | 6/2005 |
| KR | 200408926 Y1 | 2/2006 |
| WO | WO 03/028807 A1 | 4/2003 |
| WO | WO 2004/037068 A2 | 5/2004 |

* cited by examiner

[Fig. 1]
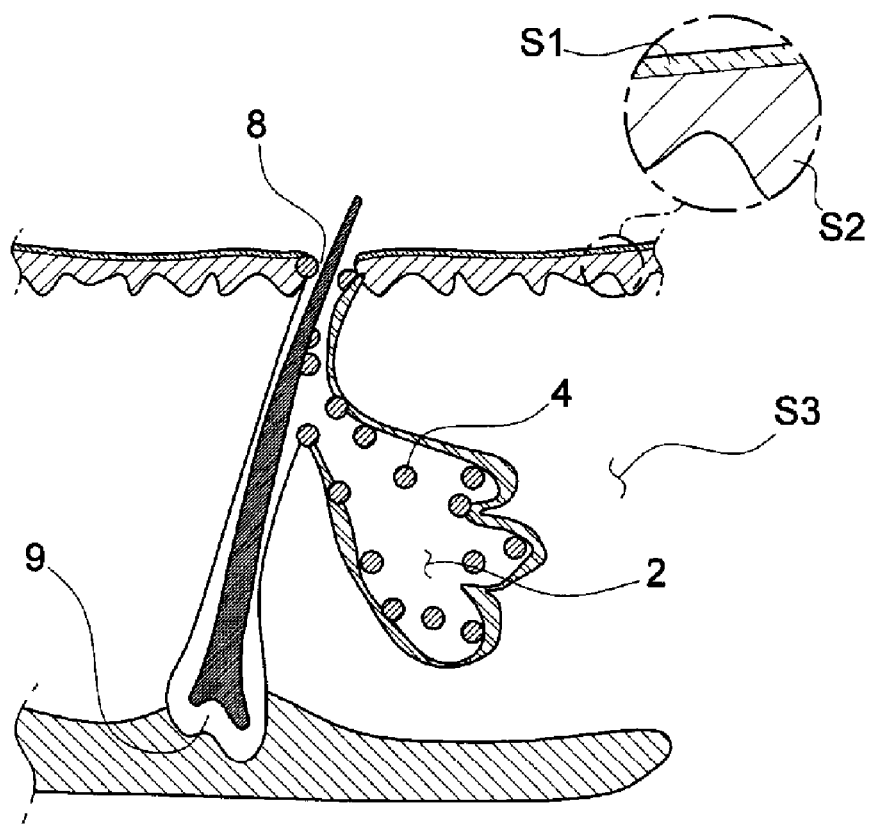
[Fig. 2]
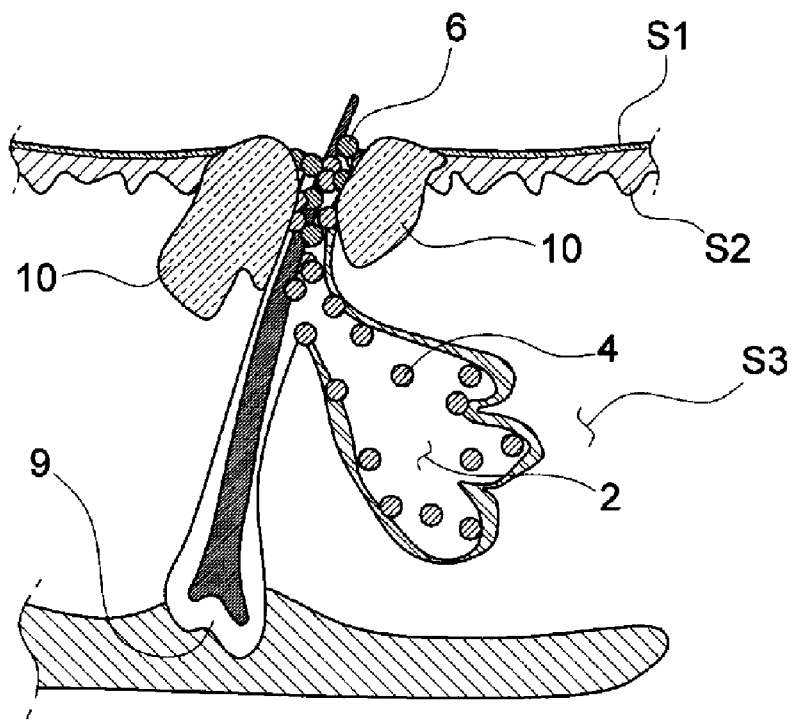

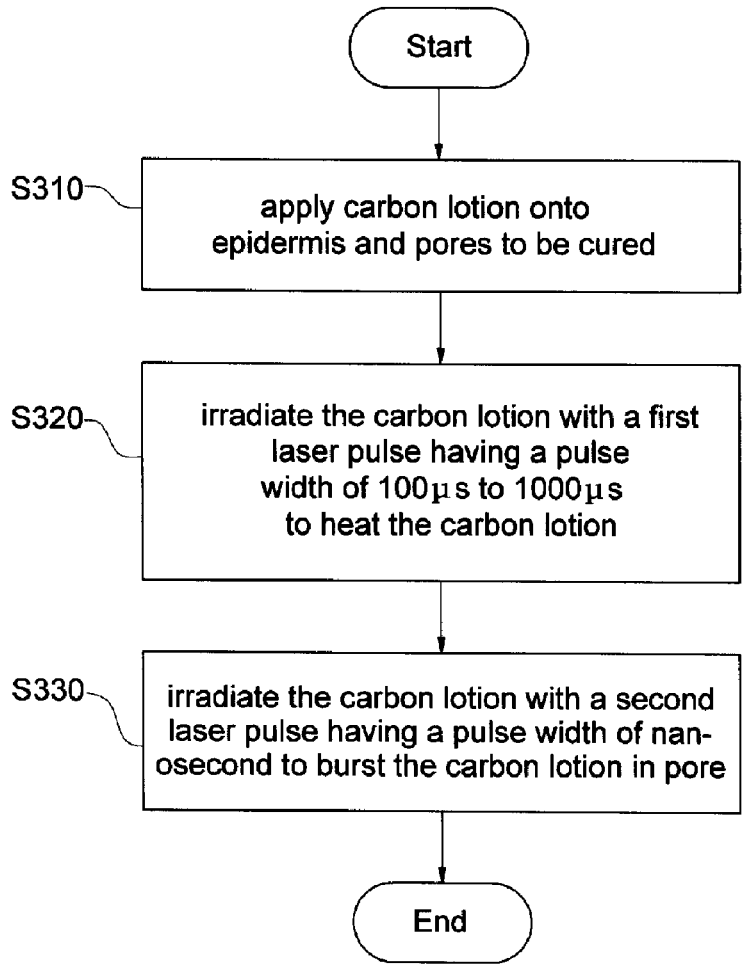
[Fig. 3]
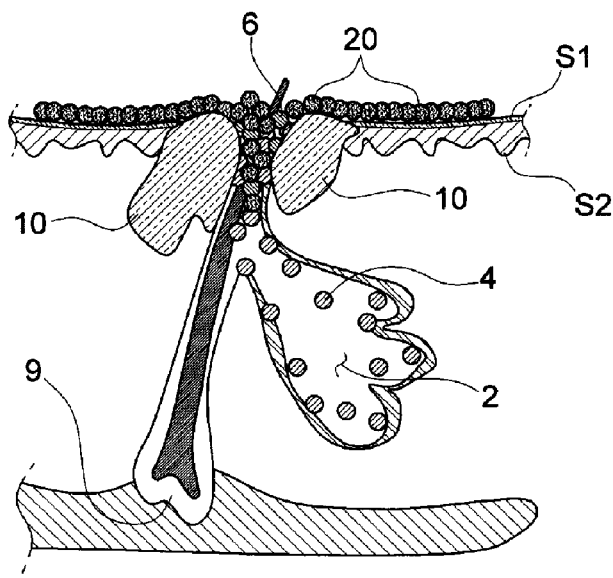
[Fig. 4]

[Fig. 5]
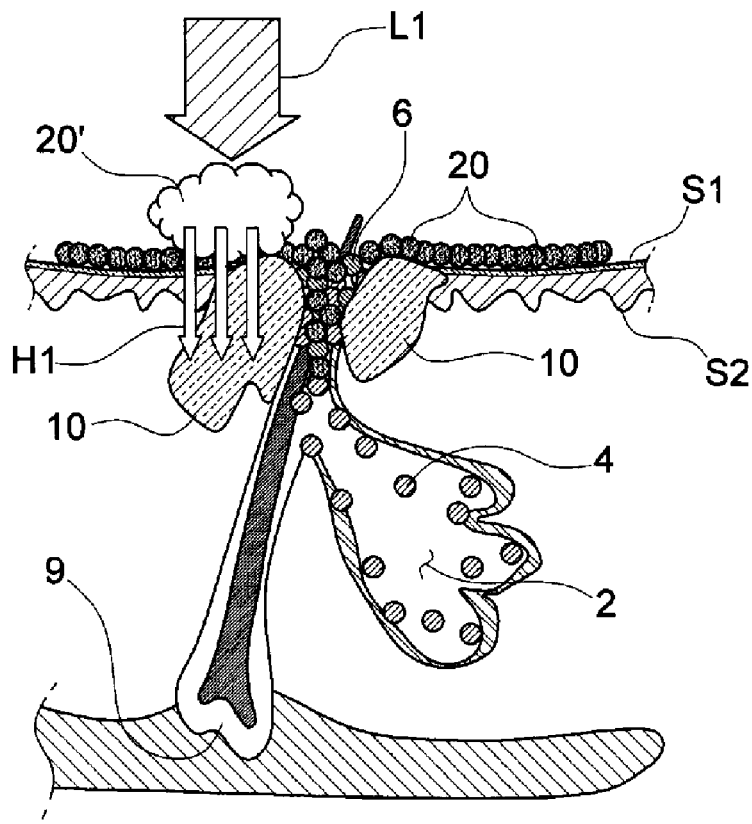
[Fig. 6]
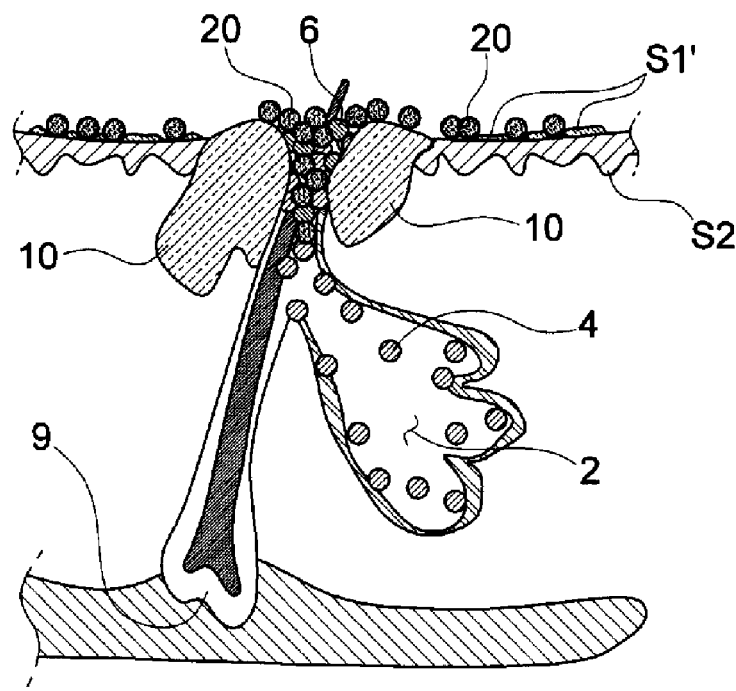

[Fig. 7]
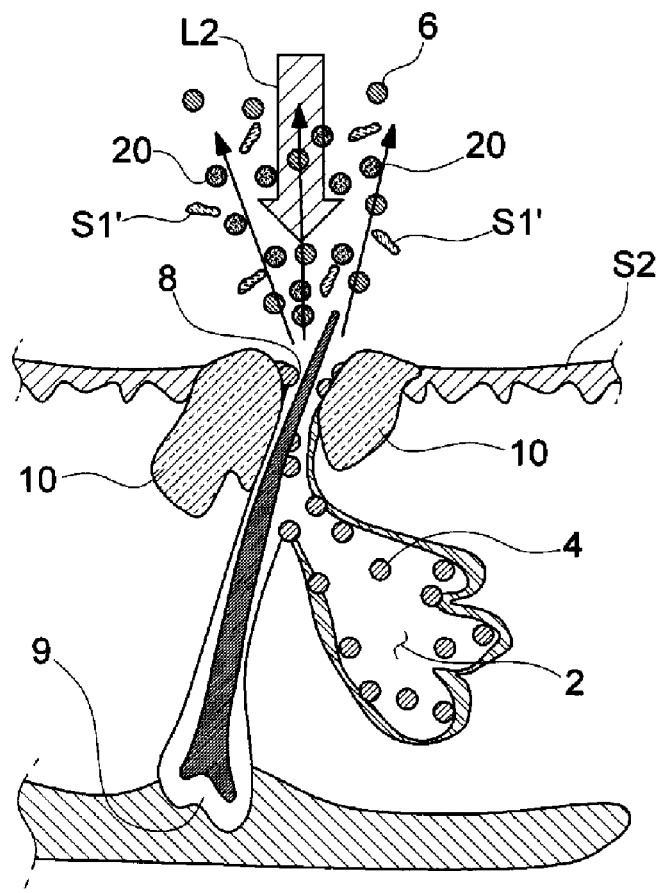
[Fig. 8]
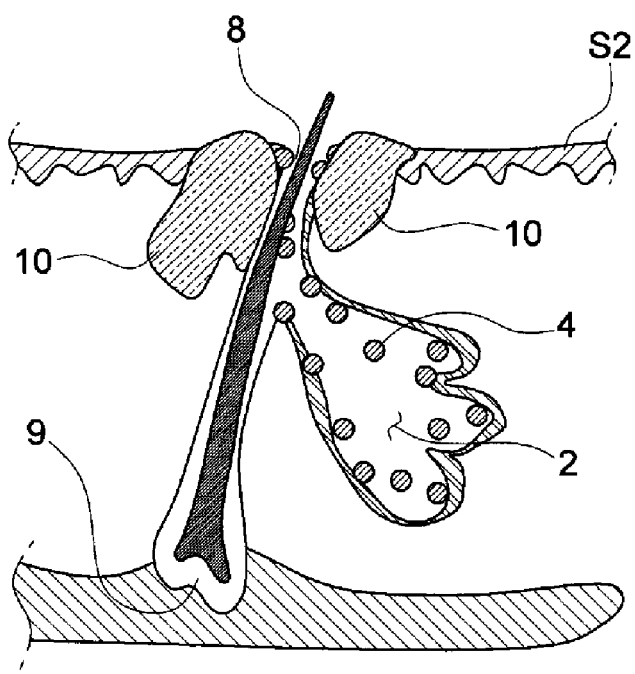

METHOD OF CURING INFLAMMATORY ACNE BY USING CARBON LOTION AND PULSED LASER

CROSS REFERENCE TO RELATED APPLICATIONS

This application is a U.S. national stage filing under 35 U.S.C. §371 of PCT Application PCT/KR2006/002043 filed May 29, 2006, which claims priority to KR 10-2005-0128505 filed Dec. 23, 2005.

TECHNICAL FIELD

The present invention relates to an acne curing method, and more particularly to a method of curing inflammatory acne by applying a carbon lotion onto a face covered with the acne, irradiating the applied carbon lotion with a laser pulse having a pulse width of microsecond, and irradiating the applied carbon lotion with a laser pulse having a pulse width of nanosecond to sterilize acne bacilli and open skin pores clogged with sebum, thereby entirely treating the inflammatory acne.

BACKGROUND ART

It is known that the onset of acne is generally caused by the following four reasons: 1) excessive production of sebum; 2) excessive cell division of follicular epithelium and thus blocking of pores; 3) production of inflammation due to proliferation of Pro-pionibacterium acne (P.acne) and generation of prefatty acid; and 4) inflammation of follicle and its surrounding area. A major factor affecting the pathogeny mechanism comprises climate or weather, season, modification of gene or hormone, skin wastes, and others.

The onset causes of the acne will be described in detail with reference to the accompanying drawings.

FIG. 1 is a cross-sectional view schematically illustrating the surrounding area of a pore, and FIG. 2 is a cross-sectional view schematically illustrating inflammatory acne developed around the pore.

Referring to FIGS. 1 and 2, if a sebum 4 is excessively secreted from a sebum gland 2, the sebum 4 is not smoothly discharged from the sebum gland 2, and thus is accumulated in a pore 8. The prefatty acid generated by Propionibacterium acne which is proliferated in the pore 8 stimulates the skin around the pore, which can cause inflammation in the wall of a hair follicle and an area around the pore.

With the inflammation, a stratum corneum S1 is abnormally proliferated around the pore 8, and edema caused by the inflammation 10 blocks the pore 8 to further obstruct the smooth discharge of the sebum. Hence, symptoms of acne are developed on the skin. In the drawings, reference numeral S2 denotes an epidermal layer, S3 denotes a dermal layer, and 9 denotes a hair root.

The acne treatment generally takes aim at one or some of four pathogeny mechanisms as described above.

The acne developed by the above reasons is generally cured by the following conventional methods:

1) a method of dosing a patient with drugs such as antibiotics, retinoids, or steroid;
2) a method of using an external application; and
3) a surgical method such as comedo extraction, chemical peeling, or the like.

However, the conventional methods have a limited effect, and give rise to several side effects.

In particular, in case of the chemical peeling in which a chemical drug is applied onto the epidermis to peel off the epidermal layer, the clogged pores are opened to allow the sebum to be smoothly discharged, and the inflamed tissues are eliminated from the skin. However, experienced operators are required, and it is not possible to precisely control a penetrated depth when the drugs are applied, thereby possibly giving rise to side effects, for example, scar or hyper-pigmentation caused by excessive peeling of the epidermal layer. Although a laser having a wavelength of about 400 nm or intense pulsed light is used to cure the acne, because it cannot open the clogged pores, a desired curing effect is not expected. Any method cannot effectively treat the acne to date.

DISCLOSURE OF INVENTION

Technical Problem

Therefore, the present invention has been made to solve the above-mentioned problems occurring in the prior art, and an object of the present invention is to provide a method of curing inflammatory acne by using a carbon lotion and a pulsed laser, in which the carbon lotion applied onto a skin is irradiated with a first laser pulse having a relatively long pulse length (i.e., microsecond), so that stratum corneum is separated from an epidermal layer of the skin so as to be easily removed from the epidermal layer, the stratum corneum is eliminated by the reaction of thermal effect, and the epidermal layer and a dermal layer are stimulated to activate generation or reorganization of cells such as collagen and thus further accelerate regeneration of the skin.

Another object of the present invention is to provide a method of curing inflammatory acne by using a carbon lotion and a pulsed laser, in which the carbon lotion applied onto a skin is irradiated with a second laser pulse having a relatively short pulse length (i.e., nanosecond), so that carbon powders existed in pores are burst out to eliminate a stratum corneum which is already separated by a first laser pulse and to open the pores and passages of the pores clogged by sebum, bacteria, keratin, or the like, through which old sebum, debris of keratin, and others are cleanly removed from the pores.

Further another object of the present invention is to provide a method of curing inflammatory acne by using a carbon lotion and a pulsed laser, in which the carbon lotion applied onto a skin is irradiated with a first laser pulse having a relatively long pulse length (i.e., microsecond) and a second laser pulse having a relatively short pulse length (i.e., nanosecond), thereby sterilizing acne bacilli such as Propionibacterium acne and thus eliminating the onset causes of acne.

Technical Solution

In order to accomplish the above-mentioned objects, there is provided a method of curing inflammatory acne by using a carbon lotion and a pulsed laser, the method comprising the steps of: applying the carbon lotion onto epidermis to be cured and pores; and irradiating the carbon lotion with a laser pulse to heat and burst the applied carbon lotion.

The irradiating step comprises irradiating the applied carbon lotion with a first laser pulse having a first pulse width to heat the carbon lotion, and irradiating the applied carbon lotion with a second laser pulse having a second pulse width shorter than the first pulse width to burst the carbon lotion in the pore, after the first laser pulse is irradiated.

Advantageous Effects

According to the present invention, the method of curing the inflammatory acne by using the carbon lotion and the pulsed laser has the following effects.

1) The carbon lotion applied onto the epidermis is irradiated with the first laser pulse having a relatively long pulse length (i.e., microsecond) and the second laser pulse having a relatively short pulse length (i.e., nanosecond), in order to simply and effectively cure the inflammatory acne.

2) The carbon lotion applied onto the epidermis is irradiated with the first laser pulse having a relatively long pulse length (i.e., microsecond), so that the stratum corneum is evenly eliminated by the heat generated from the carbon lotion, and the epidermal layer and the dermal layer are stimulated.

By stimulating the epidermal layer and the dermal layer, the generation or reorganization of cells such as collagen is activated, and thus the regeneration of the skin cells is further accelerated.

3) Through the uniform regeneration of the dermal cells, the wound is quickly closed, and it can prevent the scar due to the acne.

4) The carbon lotion applied onto the epidermis is irradiated with the second laser pulse having a relatively short pulse length (i.e., nanosecond), in order to burst out the carbon powders in the pore and thus eliminate the stratum corneum and open the pore.

Through the open of the pore, the old sebum, the debris of keratin, and others are cleanly removed from the pore, so that the passage of the pore clogged by the sebum, the bacteria, the keratin, and others is completely opened.

Since the passage of the pore is completely opened, the secretion of the sebum gland can be adjusted.

5) Since the carbon lotion applied onto the epidermis is irradiated with the first laser pulse having a relatively long pulse length (i.e., microsecond) and the second laser pulse having a relatively short pulse length (i.e., nanosecond), acne bacilli such as Propionibacterium acne are sterilized to eliminate the onset causes of acne.

6) According to the above effects, proper prognosis is obtained in the process of curing the acne.

BRIEF DESCRIPTION OF THE DRAWINGS

The above objects, other features and advantages of the present invention will become more apparent by describing the preferred embodiments thereof with reference to the accompanying drawings, in which:

FIG. 1 is a cross-sectional view schematically illustrating a surrounding area of a pore.

FIG. 2 is a cross-sectional view schematically illustrating inflammatory acne produced around a pore.

FIG. 3 is a flow diagram explaining a method of curing inflammatory acne by using a carbon lotion and a pulsed laser according to an embodiment of the present invention.

FIG. 4 is a cross-sectional view schematically illustrating the epidermis applied with a carbon lotion.

FIG. 5 is a conceptual view explaining the case a first laser pulse is irradiated onto a carbon lotion.

FIG. 6 is a view illustrating carbon powders left after a first laser pulse is irradiated.

FIG. 7 is a conceptual view explaining the case a second laser pulse is irradiated onto a carbon lotion.

FIG. 8 is a view illustrating a surround area of acne after first and second laser pulses axe irradiated.

BEST MODE FOR CARRYING OUT THE INVENTION

Now, a method of curing inflammatory acne by using a carbon lotion and a pulsed laser according to a preferred embodiment of the present invention will be described in detail with reference to the accompanying drawings.

FIG. 3 is a flow diagram explaining a method of curing inflammatory acne by using a carbon lotion and a pulsed laser according to an embodiment of the present invention, and FIG. 4 is a cross-sectional view schematically illustrating the epidermis applied with the carbon lotion.

Firstly, after the epidermis of a skin to be treated is clearly cleaned, a carbon lotion 20 (hereinafter referred to as carbon powders, since the carbon lotion consists of powders) is evenly applied onto the epidermis and pores 8 (step S310), as shown in FIGS. 3 and 4.

The applied thin carbon lotion 20 is evenly irradiated with a first laser pulse L1 having a pulse width of microsecond, preferably 100 μs to 1000 μs, by using a pulsed Nd:YAG laser (not shown) (oscillation wavelength: 1064 nm) (step S320). The reason why the carbon lotion 20 is irradiated with the relatively long pulse of microsecond is that laser energy is transferred to the carbon lotion to emit heat.

The first laser pulse L1 has a pulse length similar to a pumping time of a lamp (not shown) of the Nd:YAG laser.

The reason which the carbon lotion 20 is used an igniter is that the carbon lotion well absorbs the light of 1064 nm which is the oscillation wavelength of the Nd:YAG laser.

When the carbon lotion 20 is irradiated with the first laser to absorb the energy, the heat is generated from the carbon lotion 20, and then the carbon lotion starts to burn. The burning state of the carbon lotion 20 is designated by reference numeral 20 in FIG. 5 which is a conceptual view explaining the case the first laser pulse is irradiated onto the carbon lotion.

A stratum corneum S1 is separated from an epidermis by the heat H1 generated from the carbon lotion 20, and simultaneously, an epidermal layer S2 and a dermal layer S3 are stimulated to activate generation or reorganization of cells such as collagen and thus further accelerate regeneration of the skin. In FIG. 6 which is a view illustrating the carbon powders left after the irradiation of the first laser pulse, the stratum corneum which is partially left on the stratum corneum after it is mostly removed is indicated by reference numeral S1'.

Also, burning of the carbon lotion causes Propionibacterium acne to be sterilized. As a result, the inflammation 10 developed around the pore by the Propionibacterium acne is cured.

The carbon lotion 20 applied onto the epidermis is mostly removed by the first laser pulse L1, but the carbon powders penetrated into the pore 8 are left as it is.

FIG. 7 is a conceptual view explaining the case the second laser pulse is irradiated onto the carbon lotion.

After the acne has been treated by the first laser pulse, as shown in FIG. 7, the left carbon lotion 20 is irradiated by the second laser pulse L2 from the Nd:YAG laser (not shown) (S330). The second laser pulse L2 is a pulse wave having a pulse width shorter than that of the first laser pulse L1, preferably a short pulse length of nanosecond.

More preferably, the second laser pulse L2 has a pulse width of 5 ns to 50 ns. According to clinical tests, the best effect is obtained by the second pulse L2 having the pulse width of 5 ns to 50 ns.

When the carbon lotion 20 partially left on the epidermis and the pore 8 is irradiated by the second laser pulse from the Q-switch of the Nd-YAG laser, the carbon lotion 20 absorbs the energy of the second laser pulse having a short pulse width of nanosecond.

Since the second laser pulse has a very short pulse length, the time in which the carbon powders absorb the energy. As a result, the temperature of the carbon powders is abruptly raised.

The carbon powders with temperature abruptly raised are ruptured into small debris. If the carbon powders are burst in the pore 8, the stratum corneum S1 peeled off from the epidermis by the laser beam of the first laser pulse is completely removed therefrom.

Also, when the carbon powders are burst in the pore 8, old sebum 4, debris of keratin 6, and others, which are accumulated in the pore 8, are cleanly removed from the pore 8. As a result, passages of the pores clogged by sebum, bacteria, keratin, or the like are entirely opened.

Further, the second laser pulse L2 gives thermal stimulation to the inflammation around the pores to further accelerate the treatment of the inflammation.

After the stratum corneum S1 is removed from the epidermis by the radiation of the first laser pulse, the partially left stratum corneum S1 is entirely removed by the burst of the carbon lotion 20, thereby keeping the skin state clean and thus preventing development of the acne.

FIG. 8 is a view illustrating the surround area of the acne after the first and second laser pulses are irradiated.

Referring to FIG. 8, the burst of the carbon powders by the irradiation of the second laser pulse having a short pulse width causes the pores to open, which can keep the pores clean, and restraining the excessive secretion of sebum gland, thereby curing the acne.

Preferably, the first laser pulse L1 and the second laser pulse L2 are adapted to have energy density of 1.5 J/cm$^2$ to 3.0 J/cm$^2$, according to the clinical tests of the present invention.

With the method of curing the inflammatory acne according to the present invention, the carbon lotion 20 is irradiated with the first laser pulse having a relatively long pulse length (i.e., microsecond), so that the stratum corneum is separated from the epidermis so as to be easily removed from the epidermis, and an epidermal layer and a dermal layer are stimulated to activate generation or reorganization of cells such as collagen and thus further accelerate regeneration of the skin. Further, it sterilizes acne bacilli such as Propionibacterium acne to eliminate the inflammation 10. Then, the carbon powders are irradiated with the second laser pulse having a relatively short pulse length (i.e., nanosecond), so that the carbon powders are burst out to open the clogged pores and thus keep the pores clean, and to restrain the excessive secretion of the sebum gland and thus basically eliminate the onset causes of acne, thereby curing the acne.

In this embodiment the irradiation of the first laser pulse and second laser pulse is achieved by using the Nd:YAG laser having the Q-switch, but the present invention is not limited thereto. It is, of course, noted that the case of using a laser capable of oscillating a laser pulse of nanosecond after a laser pulse of microsecond is oscillated belongs to the scope of the present invention.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

Industrial Applicability

As apparent from the above description, the method of curing the inflammatory acne by using the carbon lotion and the pulsed laser, according to the present invention, has the following effects.

1) The carbon lotion applied onto the epidermis is irradiated with the first laser pulse having a relatively long pulse length (i.e., microsecond) and the second laser pulse having a relatively short pulse length (i.e., nanosecond), in order to simply and effectively cure the inflammatory acne.

2) The carbon lotion applied onto the epidermis is irradiated with the first laser pulse having a relatively long pulse length (i.e., microsecond), so that the stratum corneum S1 is evenly eliminated by the heat generated from the carbon lotion, and the epidermal layer S2 and the dermal layer S3 are stimulated.

By stimulating the epidermal layer and the dermal layer, the generation or reorganization of cells such as collagen is activated, and thus the regeneration of the skin cells is further accelerated.

3) Through the uniform regeneration of the dermal cells, the wound is quickly closed, and it can prevent the scar due to the acne.

4) The carbon lotion applied onto the epidermis is irradiated with the second laser pulse having a relatively short pulse length (i.e., nanosecond), in order to burst out the carbon powders in the pore and thus eliminate the stratum corneum S1 and open the pore.

Through the open of the pore, the old sebum, the debris of keratin, and others are cleanly removed from the pore 8, so that the passage of the pore 8 clogged by the sebum, the bacteria, the keratin, and others is completely opened.

Since the passage of the pore 8 is completely opened, the secretion of the sebum gland can be adjusted.

5) Since the carbon lotion applied onto the epidermis is irradiated with the first laser pulse having a relatively long pulse length (i.e., microsecond) and the second laser pulse having a relatively short pulse length (i.e., nanosecond), acne bacilli such as Propionibacterium acne are sterilized to eliminate the onset causes of acne.

6) According to the above effects, proper prognosis is obtained in the process of curing the acne.

The invention claimed is:

1. A method of curing inflammatory acne by using a carbon lotion and a pulsed laser, the method comprising:
    applying the carbon lotion onto epidermis and pores to be cured; and
    irradiating the applied carbon lotion with a first laser pulse having a first pulse width to heat the applied carbon lotion; and
    irradiating the applied carbon lotion with a second laser pulse having a second pulse width shorter than the first pulse width to burst the carbon lotion in the pores after the first laser pulse is irradiated,
    wherein the first pulse width is in a range of 100 µs to 1000 µs,
    wherein the second pulse width is in a range of 5 ns to 50 ns,
    wherein each of the first and second pulses have an energy density in a range from 1.5 J/cm2 to 3.0 J/cm2,
    wherein a laser producing the first and second laser pulses has an oscillation wavelength of 1064 nm.

2. The method as claimed in claim 1, wherein the laser comprises an Nd:YAG laser.

3. The method as claimed in claim 1, wherein the laser comprises a pulsed Nd:YAG laser.

4. The method as claimed in claim 1, wherein the laser comprises an Nd:YAG laser with a Q-switch.

5. The method as claimed in claim 4, wherein irradiating the applied carbon lotion with a second laser pulse comprises irradiating the applied carbon lotion with the second laser pulse by the Q-switch after the applied carbon lotion is irradiated with the first laser pulse.

* * * * *